United States Patent [19]

Sano et al.

[11] Patent Number: 5,270,663

[45] Date of Patent: Dec. 14, 1993

[54] APPARATUS FOR DETECTING A LIQUID MIXING RATIO

[75] Inventors: Yoshihiko Sano, Okazaki; Hisataka Okado, Chita; Masahiko Miyahara, Chiryu; Hiroaki Nishimura, Okazaki; Ichiro Hosotani, Numazu; Yoshiki Chujo, Mishima, all of Japan

[73] Assignees: Nippondenso Co., Ltd., Kariya; Toyota Jidosha Kabushiki Kaisha, Toyota, both of Japan

[21] Appl. No.: 906,864

[22] Filed: Jul. 1, 1992

[30] Foreign Application Priority Data

Jul. 3, 1991 [JP] Japan .................................. 3-163048
May 15, 1992 [JP] Japan .................................. 4-123837

[51] Int. Cl.$^5$ ........................................... G01R 27/26
[52] U.S. Cl. .................................... 324/676; 324/442; 324/663; 324/698; 324/704; 324/710
[58] Field of Search ............... 324/439, 442, 663, 676, 324/677, 686, 693, 698, 704, 710, 711; 204/406

[56] References Cited

U.S. PATENT DOCUMENTS

| | | | |
|---|---|---|---|
| 3,593,118 | 7/1971 | Chaney et al. | 324/442 X |
| 3,816,811 | 6/1974 | Cmelik | 324/698 X |
| 4,407,100 | 9/1977 | Robinson | 324/442 X |
| 4,470,300 | 9/1984 | Kobayashi | 324/677 X |
| 5,033,293 | 7/1991 | Honma et al. | 73/118.1 |

FOREIGN PATENT DOCUMENTS

| | | |
|---|---|---|
| 62-660849 | 9/1987 | Japan . |
| 64-80848 | 3/1989 | Japan . |
| 1-318948 | 12/1989 | Japan . |
| 2-16054 | 2/1990 | Japan . |
| 2-17650 | 2/1990 | Japan . |
| 2-17652 | 2/1990 | Japan . |
| 2-103264 | 8/1990 | Japan . |

Primary Examiner—Kenneth A. Wieder
Assistant Examiner—Glenn W. Brown
Attorney, Agent, or Firm—Cushman, Darby & Cushman

[57] ABSTRACT

A liquid mixing ratio detecting apparatus is designed so that an oscillation voltage generated by an oscillation unit is applied to one of a differentiating circuit and an integrating circuit, which is constituted by a combination of a capacitor composed of a pair of opposite electrodes for detecting a mixing ratio of a mixed liquid and a resistor, and a mixing ratio detecting unit produces a signal relating to an inclination rate of one of a differential waveform signal and an integration waveform signal, which is generated by one of the differentiating circuit and the integrating circuit, respectively, thereby obtaining a signal representing the mixing ratio of the mixed liquid on the basis of the produced signal relating to the inclination rate of the waveform signal.

9 Claims, 8 Drawing Sheets

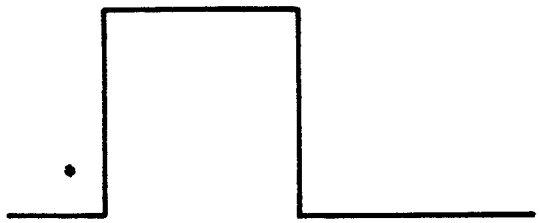
FIG. 2A
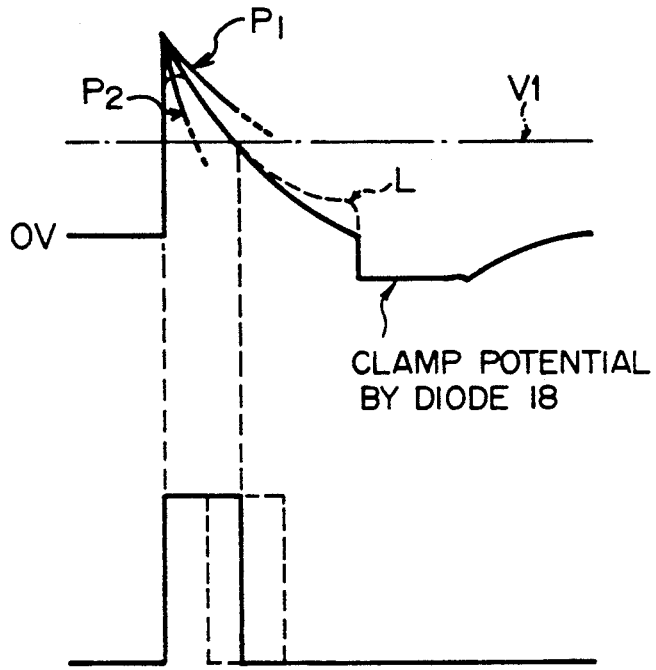
FIG. 2B
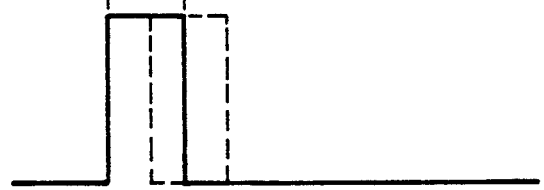
FIG. 2C
FIG. 3
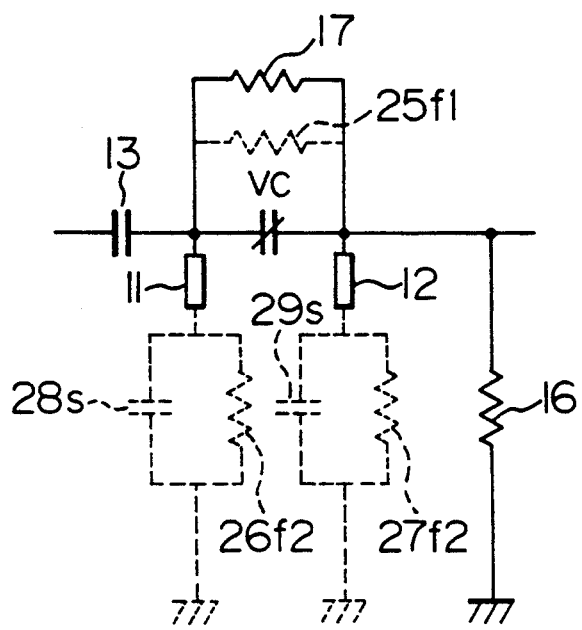

APPARATUS FOR DETECTING A LIQUID MIXING RATIO

BACKGROUND OF THE INVENTION

The present invention relates to a liquid mixing ratio detecting apparatus for detecting a liquid mixing ratio of a mixed liquid such as an apparatus for measuring a concentration of alcohol mixed in gasoline fuel, and more particularly to a liquid mixing ratio detecting apparatus having a pair of electrodes immersed in the mixed liquid to be utilized as a capacitor.

A prior art liquid mixing ratio detecting apparatus will hereinafter be described by taking an apparatus for detecting a mixing ratio of a mixture of gasoline and alcohol as an example. In foreign countries, gasoline fuel having alcohol mixed in gasoline (hereinafter abbreviated as alcohol mixed gasoline) is used as mixed fuel. Such mixed fuel has an air-fuel ratio different from pure gasoline fuel. As a result, there exist differences in a fuel injection amount and ignition timing therebetween.

In general, the fuel injection amount is obtained by multiplying a basic fuel injection amount by a coefficient corresponding to the air-fuel ratio. Further, the air-fuel ratio is generally about 15:1 for pure gasoline, and it is about 6:1 for 100% alcohol. As a result, there results the alcohol concentration versus air-fuel ratio characteristics in which the proportion of air decreases as an alcohol concentration increases. According to the alcohol concentration versus air-fuel ratio characteristics, in the case of alcohol mixed gasoline, it is necessary to change the air-fuel ratio in accordance with an alcohol concentration in the fuel tank and consequently to change the coefficient by which the basic fuel injection amount is multiplied.

As a liquid mixing ratio detecting apparatus for detecting a concentration of alcohol in alcohol mixed gasoline, there is known a system in which a pair of electrodes are immersed in the alcohol mixed gasoline and are used to detect electrostatic capacitance formed between the pair of electrodes (hereinafter referred to simply as "capacitance"). That is, since there is a great difference in the magnitude of dielectric constant between alcohol and gasoline (the dielectric constant of alcohol is 33.6 and that of gasoline is 2), a change of capacitance between the two electrodes depending on a content ratio of alcohol and gasoline is utilized. More specifically, as shown in FIG. 10, a pair of electrodes 1 and 2 are disposed in a pipeline 4 of alcohol mixed gasoline, for example, so as to be immersed in the alcohol mixed gasoline, and the electrodes 1 and 2 are connected to an oscillation circuit 3. An oscillation output of the oscillation circuit 3 is converted into a voltage (shown by Vs) through a frequency/voltage converter 5.

An example of a conventional apparatus employing the above-described system is disclosed in JP-B-2-103264. The liquid mixing ratio detecting apparatus disclosed in the above laid-open utility model application is designed so that the pair of electrodes 1 and 2 are used as a constituent element of a resonance circuit in the oscillation circuit 3, and it is arranged to detect a change of an oscillation frequency due to a change of electrostatic capacitance based on a change of dielectric constant caused by a change of a concentration of alcohol.

However, in the liquid mixing ratio detecting apparatus disclosed in the above laid-open application, there arises a problem in that, because metal ions and impurities are dissolved in the mixed fuel from inner wall members of a fuel tank and/or a pipeline thereby to change the conductivity of the mixed fuel, accurate detection is difficult to be performed. This is because that, in the sensor disclosed in the above laid-open application, as shown in FIG. 10 by dotted lines, a resistor Rf1, whose resistances value is determined by the conductivity of the mixed fuel and the structure of the electrodes 1 and 2, is present between the electrodes 1 and 2, and similarly a resistor Rf2 and a capacitors Cs are present between the electrodes 1, 2 and the pipeline 4, and thus metal ions and impurities dissolved in the mixed fuel act to reduce the resistance value of the resistors Rf1 and Rf2 and the capacitance value of the capacitor Cs, especially the resistance value of the resistor Rf1, and, as a result, it becomes difficult to obtain desired information only from the magnitude of the capacitance between the electrodes 1 and 2.

Besides, since the electrodes 1 and 2 in FIG. 10 are used as constituent elements of the resonance circuit of the oscillation circuit 3, in order to perform accurate detection, it is essential that the capacitor of the resonance circuit has a small leakage current. However, when the conductivity of the mixed fuel is increased, then Rf1 and Rf2 are decreased and hence a leakage current is increased, thereby to increase a detection error. Further, it is considered that, since oscillation conditions are not satisfied, a reduction in an oscillation output and even stoppage of oscillation occur, and, as a result, the detection becomes difficult to be performed.

The present invention is intended to solve the above-described problems, and it is an object of the present invention to provide a liquid mixing ratio detecting apparatus in which an electrode capacitor is not used as a constituent element of an oscillation circuit, but is used as a capacitor for determining an inclination rate of a differential waveform or an integral waveform, and besides which is constructed to reduce an influence of a leakage current on an inclination rate signal, thereby reducing an adverse influence of a change of the conductivity of the mixed fuel.

SUMMARY OF THE INVENTION

The liquid mixing ratio detecting apparatus of the present invention is constructed to comprise: a pair of electrodes immersed with a predetermined distance kept therebetween in a mixed liquid containing a plurality of liquids having respective dielectric constants which are different from each other; a capacitor for detecting a mixing ratio whose capacitance varies depending on a mixing ratio of the mixed liquid; a resistor for constituting, in conjunction with the capacitor, one of a differentiating circuit and an integrating circuit; oscillation means for applying an oscillation signal of a fixed frequency to one of the differentiating circuit and the integrating circuit; and mixing ratio detecting means for detecting an inclination rate signal relating to an inclination rate of one of a differential waveform and an integration waveform of the oscillation signal generated by one of the differentiating circuit and the integrating circuit, respectively, and outputting a mixing ratio signal relating to the mixing ratio of the mixed liquid on the basis of the detected inclination rate signal.

A first preferred aspect of the present invention further comprises a second resistor connected across the pair of electrodes.

In a second preferred aspect of the present invention, alcohol mixed gasoline is used as the mixed liquid.

In a third preferred aspect of the present invention, an oscillation voltage of a fixed frequency is applied from the oscillation means to one of the pair of electrodes, and the resistor is connected between the other of the pair of electrodes and a reference potential point of the apparatus to constitute, in conjunction with the capacitor, the differentiating circuit. Further, the oscillation means may be constructed as a rectangular waveform oscillation circuit and the mixing ratio detecting means may be constructed as a comparator which produces a signal voltage proportional to a period of time between two points on the differential waveform of the rectangular waveform, which have respective predetermined potentials equal to each other, as the mixing ratio signal. Further, a third resistor may be connected between the above-mentioned one of the pair of electrodes and an output terminal of the oscillation circuit. Further, a DC blocking capacitor may be connected between at least one of the output terminal of the oscillation circuit and the resistor, and a corresponding electrode of the pair of electrodes.

In the liquid mixing ratio detecting apparatus of the present invention, a capacitor, which detects a mixing ratio and is composed of a pair of electrodes immersed in the mixed liquid with a predetermined distance kept therebetween, and a resistor form a differentiating circuit or an integrating circuit which outputs a differential waveform or an integral waveform of an input signal, respectively. The oscillation means applies an output oscillation signal of a fixed frequency to the differentiating circuit or the integrating circuit, and the mixing ratio detecting means detects an inclination rate signal relating to an inclination rate of the differential waveform or relating to that of the integral waveform which is obtained by differentiating or integrating the oscillation signal in the differentiating circuit or the integrating circuit, respectively, and the mixing ratio detecting means outputs a mixing ratio signal relating to a liquid mixing ratio of the mixed liquid on the basis of the inclination rate signal.

That is, if a dielectric constant of each of the liquids is known, the mixing ratio of the mixed liquid is obtained on the basis of the dielectric constant of the mixed liquid. The inclination rate signal is a function of a time constant CR of the differentiating circuit or the integrating circuit, and C of the time constant CR is proportional to the dielectric constant of the mixed liquid. Consequently, the inclination rate signal becomes a function of the dielectric constant of the mixed liquid, and hence the mixing ratio of the mixed liquid can be obtained from a result of measurement of the inclination rate signal.

In the case where an electrode capacitor is used as a constituent element of a resonance circuit in the oscillation circuit, a leakage current caused by an increase in the conductivity of the mixed liquid gives rise to a change of the oscillation frequency, and moreover, when the oscillation conditions are not satisfied, the oscillation of the oscillation circuit is stopped, which makes the detection impossible. By contrast, in the case where the electrode capacitor is used as a constituent element of a differentiating circuit or an integrating circuit, even if metal ions, impurities and the like are dissolved in the mixed liquid from inner wall members of a tank and a pipeline, resulting in an increase in a leakage current to some extent, the detection can be performed so far as the inclination rate signal can be obtained.

The second resistor connected in parallel with the pair of electrodes forms a current path separately from the mixed liquid between the pair of electrodes, and it causes the leakage current to flow therethrough. Therefore, even if the conductivity of the mixed fuel is changed, an influence of that change on the differential waveform or the integral waveform can be reduced. Thus, the mixing ratio can be detected with elevated precision.

In the case where the differentiating circuit is formed by a combination of the capacitor for detection and the resistor, if the oscillation means has a construction of a rectangular waveform oscillating circuit, a mixing ratio signal is obtained to have a value proportional to a period of time between two points on the differential waveform of the rectangular waveform, which have respective predetermined potentials equal to each other, and this value can be converted to a signal voltage by the comparator.

Further, the provision of the third resistor makes fine adjustment of an output of the oscillation circuit possible, and this fine adjustment makes it possible to reduce an influence of a change of the conductivity of the mixed fuel.

Further, the DC blocking capacitor can prevent corrosion of the electrodes for detection from being caused by a DC current.

The apparatus of the present invention can be used to detect a mixing ratio of a mixed fuel in an internal combustion engine using alcohol mixed gasoline as the mixed fuel, whereby it is possible to satisfactorily control an amount of fuel injection, ignition timing and the like which are related to the mixing ratio of the mixed fuel.

BRIEF DESCRIPTION OF THE DRAWINGS

FIGS. 2A to 2C are waveform diagrams showing waveforms appearing at several portions of the apparatus shown in FIG. 1.

FIG. 3 is a circuit diagram for explaining an influence of conductivity of the mixed fuel and stray capacitances on the present invention.

DESCRIPTION OF THE PREFERRED EMBODIMENTS

A first embodiment of a liquid mixing ratio detecting apparatus of the present invention will hereinafter be described with reference to FIG. 1. The liquid mixing ratio detecting apparatus of the present embodiment is, similarly to the sensor as described above, designed so as to detect a change of capacitance existing between a pair of electrodes on the basis of a difference in dielectric constant between alcohol and gasoline.

Figure 1:
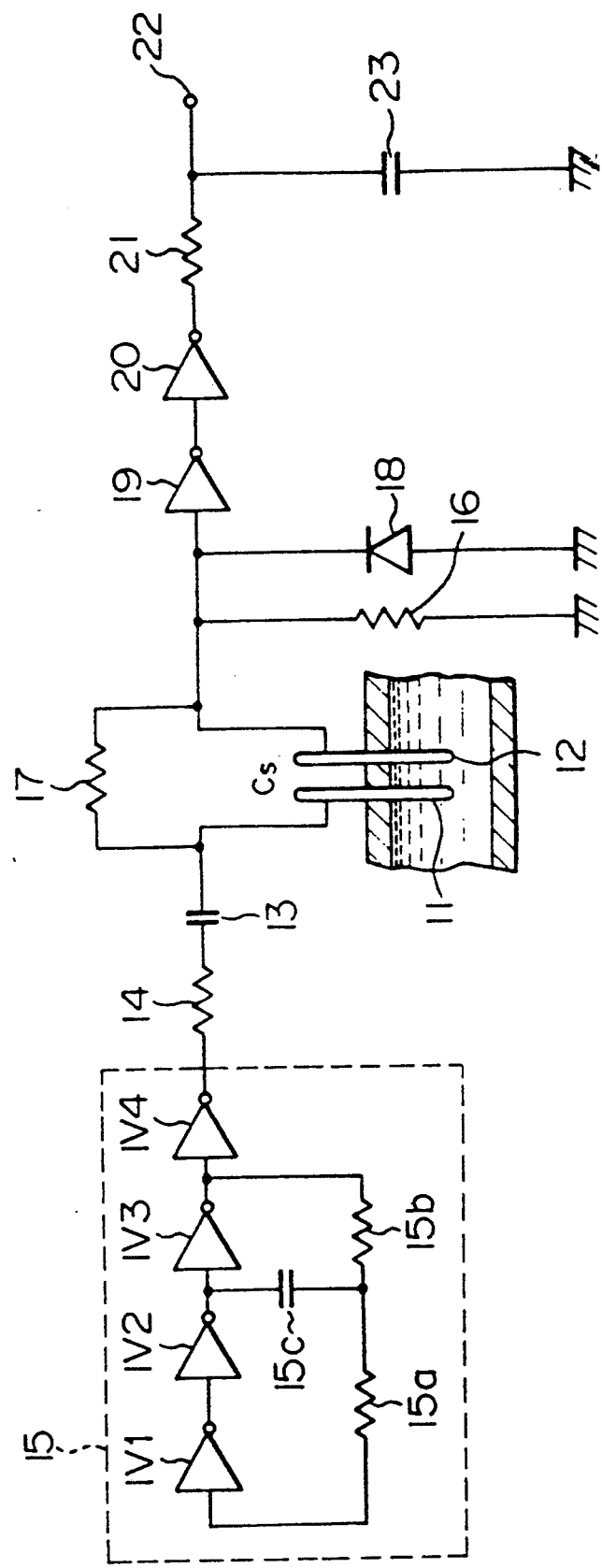
FIG. 1 is a circuit diagram showing the construction of a liquid mixing ratio detecting apparatus of a first embodiment of the present invention.

In FIG. 1, reference numerals 11 and 12 designate a pair of electrodes which are immersed in a liquid of alcohol mixed gasoline so as to be utilized as a capacitor for detecting a mixing ratio. In the electrodes 11 and 12, the input side electrode 11 is connected to an output terminal of an oscillation circuit 15 (referred to as oscillation means in the present invention) which supplies a pulse signal having a fixed frequency, e.g., 2 MHz in the present embodiment through an AC coupling (DC blocking) capacitor 13 and a third resistor 14. Incidentally, the oscillation frequency is not necessarily limited to 2 MHz. The output side electrode 12 is connected to a reference potential point (shown as an earth potential point in the embodiment of FIG. 1) through a first resistor 16 (simply referred to as a resistor in the present invention). The first resistor 16 and the capacitor formed by the electrodes 11 and 12 constitute a differentiating circuit in which the capacitor between the electrodes 11 and 12 is used as a differentiating capacitor. The differentiating circuit serves to differentiate a pulse signal supplied from the oscillation circuit 15. In parallel with the first resistor 16 connected is a diode 18 which serves to select only the positive side of the differential waveform. Further, a second resistor 17 is connected in parallel with the electrodes 11 and 12. The second resistor 17 is connected in this way knowing that the function of the electrodes 11 and 12 as a capacitor is deteriorated, while, the purpose of connection of the resistor 17 is to reduce a change of an output potential due to a variation of the conductivity of the mixed fuel. For this reason, in the present embodiment, a resistance value of the second resistor 17 is set to have a value approximately 0.2-1.0 times as large as a resistance value between the electrodes 11 and 12 which is determined by the fuel conductivity between the electrodes 11 and 12. It should be noted that an output voltage of the differential waveform is required to cross a threshold level (0.5 Vcc, where Vcc denotes a maximum value of an output voltage of the oscillation circuit 15) of inverters 19 and 20 (referred to as mixing ratio detecting means in the present invention) which will be described later. Thus, a resistance value of the second resistor 17 is preferably set to have a value about 1 to 5 times as large as the resistance value of the first resistor 16. Further, the third resistor 14 is provided in order to reduce a change of an output analog voltage due to a change of the mixed fuel conductivity which change would still remain even when the second resistor 17 is connected as described above. Here, the above-mentioned output analog voltage denotes a final output analog voltage which is obtained at an output terminal 22 as described later. In the present embodiment, the capacitor 13 has a capacitance value 100 or more times as large as a capacitance value of the capacitor formed between the electrodes 11 and 12, and it functions to block a DC current.

The oscillation circuit 15 is a ring oscillator mainly composed of four stages of inverters IV1 to IV4. An output of the third stage inverter IV3 and an input to the first stage inverter IV1 are connected by series-connected resistors 15a and 15b. A capacitor 15c for performing oscillation is connected between the junction point of the series-connected resistors 15a and 15b and an output of the second stage inverter IV2. This circuit performs an oscillating operation, since the phase of an output of the third stage inverter IV3 does not coincide with that of an input to the first stage inverter IV1. Incidentally, the fourth stage inverter IV4 is provided for the purpose of waveform shaping.

A differential waveform voltage developed across the first resistor 16 is inputted to series-connected inverters 19 and 20. The series-connected inverters 19 and 20 are inverters having a threshold level set so that, when an input voltage exceeds a predetermined threshold voltage V1, a signal of low level is outputted, while, when the input voltage does not exceed the predetermined threshold voltage V1, a signal of high level is outputted. Thus, the inverters 19 and 20 function to convert a signal having a differential waveform outputted from the differentiating circuit to a binary signal (a signal having a rectangular waveform) by using the threshold voltage V1. Thus, the inverters 19 and 20 produce a pulse signal having a rectangular waveform which is inverted at a crossing point of the threshold voltage V1 and the differential waveform. Incidentally, the above-mentioned threshold voltage V1 is about half a power source voltage applied to the inverters 19 and 20.

An output terminal of the inverter 20 is connected to an output terminal 22 through a resistor 21 for performing integration. An integrating capacitor 23 is connected between the output terminal 22 and earth. As a result, an integration voltage of an output voltage of the inverter 20 is obtained at the output terminal 22 in the form of an analog voltage representing the alcohol concentration.

The liquid mixing ratio detecting apparatus having the above-described construction can detect a concentration of alcohol in the alcohol mixed gasoline in accordance with the following operation. First, a description will be made of a case where the third resistor 14 is not provided.

The pulse signal outputted from the oscillation circuit 15 is introduced to the input side electrode 11 in the pair of electrodes 11 and 12 through the AC coupling capacitor 13. A differential waveform voltage having an inclined waveform, whose inclination rate depends on a time constant determined by the capacitance existing between the electrodes 11 and 12 and the resistance of the first resistor 16, is produced across the first resistor 16.

Further, the second resistor 17 is connected in parallel with the electrodes 11 and 12, and thus it acts as a parallel resistor with respect to the capacitor formed by the electrodes 11 and 12. Thus, this construction is designed intentionally to cause the range, in which an inclination change of the inclined waveform occurs, to be narrowed in the vertical direction (i.e. in the amplitude direction).

FIGS. 2A to 2C are waveform diagrams for explaining the function of the second resistor 17, in which FIG. 2A shows a rectangular pulse signal outputted from the oscillation circuit 15, and FIG. 2B shows a differential waveform signal (representing an inclination rate signal of the present invention) provided at the junction point of the electrode 12 and the resistor 16.

Now, if the conductivity of the mixed fuel, which is a disturbance variable, is increased and accordingly the resistance value between the electrodes 11 and 12 is decreased, an inclination rate of the differential waveform signal is correspondingly changed in the various way so that it has an adverse influence on the measurement result. Then, the second resistor 17 is connected in parallel with the capacitor formed by the electrodes 11 and 12, and the resistance value of the second resistor 17 is set to have a value 0.2 to 1.0 times as large as the resistance value (e.g., 10 K$\Omega$) between the electrodes 11 and 12. With this arrangement, as shown in FIG. 2B by a broken line L, for example, the leading edge portion of the differential waveform signal is damped and the trailing edge portion thereof is raised, so that, as a whole, the range of an inclination change of the inclined waveform portion L is deteriorated. As a result, as will be described later, a change of the inclination rate due to a change of the mixed fuel conductivity is reduced.

Next, the negative side of the differential waveform signal is cut off by the diode 18 as shown in FIG. 2B. This arrangement is adopted in order to protect the subsequent stage of inverters 19 and 20. The differential waveform signal having only the positive side voltage is converted to a binary signal by the use of the threshold voltage V1 set to the inverters 19 and 20. The threshold voltage V1 is set, for example, to a potential crossing horizontally about the center of the inclined waveform portion L, as shown by an alternate long and short dash line.

As a result, a rectangular pulse signal shown in FIG. 2C, which is inverted at the point where the threshold level V1 crosses the differential waveform voltage, is formed as an output signal from the inverters 19 and 20. If an alcohol concentration is changed, an inclination of the inclined waveform portion L of each of the differential waveform signals P1 and P2 is changed as shown in FIG. 2B, and a pulse width of the rectangular pulse signal is changed as shown by a dotted line shown in FIG. 2C. Therefore, by integrating the pulse-shaped voltage shown in FIG. 2C by the use of the integrating circuit composed of the integrating resistor 21 and the integrating capacitor 23, an analog voltage having a magnitude representing an alcohol concentration is obtained.

Thus, in the present embodiment, if the capacitance value of the capacitor formed between the electrodes 11 and 12, which are immersed in the liquid of alcohol mixed gasoline, is changed due to a change of the alcohol concentration, an inclination of the inclined waveform portion L of the differential waveform signal developed across the first resistor 16 is changed, the crossing point of the inclined waveform portion L and the threshold level V1 is shifted, and a pulse width of a resultant pulse-shaped signal is changed. Therefore, an analog voltage which is obtained by integrating the pulse-shaped voltage represents an alcohol concentration. Thus, the electrodes 11 and 12 in the present liquid mixing ratio detecting apparatus do not act as oscillation elements of the oscillation circuit 15. Therefore, it is possible to obtain an excellent meritorious effect in that a bad influence, which occurs when metal ions, impurities and the like are dissolved from inner wall members of the fuel tank and the pipeline in the mixed liquid and thereby increase the mixed fuel conductivity of the like, can be alleviated by processing the differential waveform signal, as described above.

Further, in the detection system using FM modulation, which has been explained in the description of a conventional apparatus, a loss in the capacitor formed between the electrodes 11 and 12 is required to be small in order to maintain a stable oscillating operation, and oscillation conditions are greatly changed by a change of the mixed fuel conductivity. As a result, the oscillation may be stopped in some cases. Those disadvantages of the conventional apparatuses can be overcome by the present embodiment.

Figure 10:
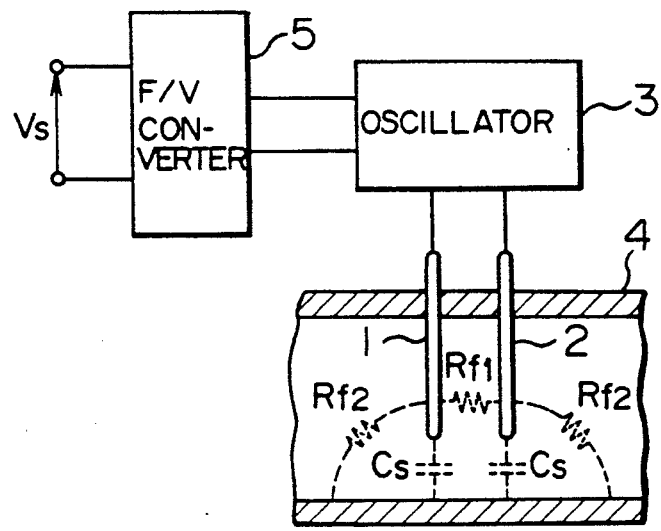
FIG. 10 is a block diagram for explaining a conventional liquid mixing ratio detecting apparatus.

Now, in the present liquid mixing ratio detecting apparatus as well, if metal ions, impurities and the like are dissolved to increase the mixed fuel conductivity, the same disadvantages as those described referring to FIG. 10 will occur. FIG. 3 shows interelectrode resistance Rf1 which is present between the electrodes 11 and 12, and floating resistance Rf2 and floating capacitance Cs which are present between the electrodes 11, 12 and the pipe wall (illustrated with dotted lines). That is, as shown in FIG. 3, a capacitor formed between the electrodes 11 and 12 is indicated by a variable capacitor Vc, and there exist inter-electrode resistance 25$f1$ between the pair of electrodes 11 and 12, a parallel combination of floating resistance 26$f2$ and floating capacitance 28$s$ between the input side electrode 11 and the reference potential point (the apparatus body), and a parallel combination of floating resistance 27$f2$ and floating capacitance 29$s$ between the output side electrode 12 and the reference potential point.

When the mixed fuel conductivity is increased, the inter-electrode resistance 25$f1$ is decreased, so that the electrodes 11 and 12 do not provide information relating only to the capacitor Vc. Further, when the floating resistance 26$f2$ and 27$f2$ which exist on the sides of the input side electrode 11 and the output side electrode 12, respectively, are decreased, the amplitude of a pulse signal outputted from the oscillation circuit 15 is decreased and also the waveform thereof is deteriorated (damped waveform), and the amplitude of the differential waveform signal is reduced. Then, the second resistor 17 is connected across the electrodes 11 and 12. With this construction, even if the inter-electrode resistance 25$f1$ is decreased, as described with reference to FIG. 2A, the connection of the second resistor 17 makes degradation of the inclination of the inclined waveform portion L due to a decrease of the inter-electrode resistance 25$f1$ unnoticeable, thereby to prevent an adverse influence from being exerted on a change of the inclination of the inclined waveform portion L caused by a change of an alcohol concentration, so that an inclination rate of the inclined waveform portion L is mainly determined by a change of the capacitance value of the capacitor Vc formed between the electrodes 11 and 12.

Next, if the mixed fuel conductivity is increased as described above, the floating resistance 26$f2$ and 27$f2$ existing on the respective sides of the input side electrode 11 and the output side electrode 12 are decreased, and the amplitude of the pulse signal outputted from the oscillation circuit 15 is decreased, and, as a result, the level of the output analog voltage is reduced. In order to overcome this disadvantage, in the same manner as the first resistor 16, by providing the third resistor 14, the amplitude of the pulse signal of a predetermined frequency outputted from the oscillation circuit 15 is suppressed intentionally and thereby deterioration of the amplitude of the inclined waveform portion L due to an increase of the mixed fuel conductivity is made to be unnoticeable.

Figure 4:
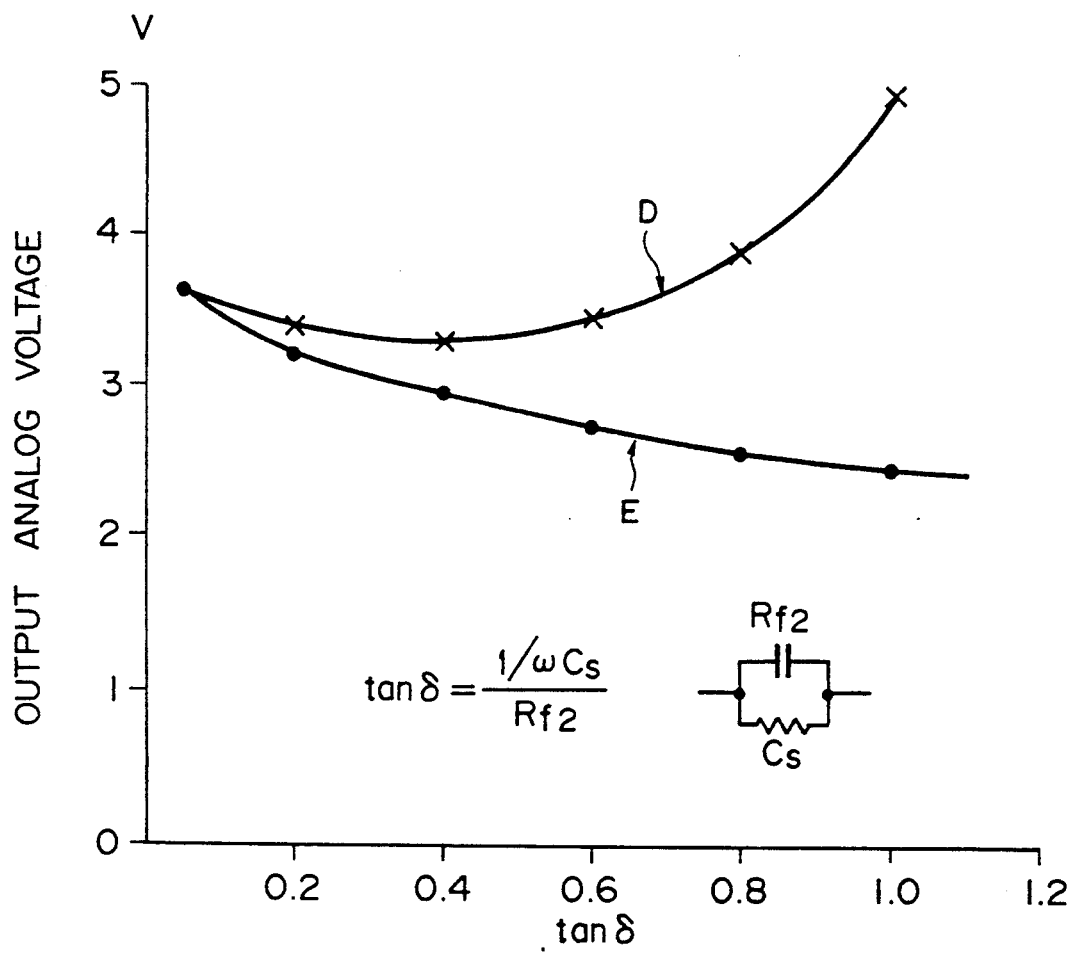
FIG. 4 is a characteristic diagram showing the relationship between the mixed fuel conductivity (represented by a loss in the electrode capacitor) and an output analog voltage.

FIG. 4 is a characteristic diagram showing the relationship between the conductivity of the mixed fuel and an output analog voltage with reference to the oscillation circuit 15 (E) having a high output impedance and the oscillation circuit 15 (D) having a low output impedance. The mixed fuel conductivity is plotted on the abscissa being converted to tan $\delta$ of the parallel combination of the floating capacitance Cs and the floating resistance Rf2. In this connection, the value of tan $\delta$ is increased as the mixed fuel conductivity is increased and hence the floating resistance Rf2 is decreased. The curve D, in which an output analog voltage is increased as tan $\delta$ is increased, is obtained in the oscillation circuit having a low output impedance (about 50 $\Omega$). On the other hand, the curve E is obtained in the oscillation circuit having a high output impedance (about 300 $\Omega$). From those characteristic curves, it is readily understood that the oscillation circuit having a low output impedance shows a correction effect of making the output analog voltage level flat as the mixed fuel conductivity is increased. Thus, a reduction in the amplitude of the inclined waveform portion caused by the floating resistance Rf2 and the floating capacitor Cs becomes greater when an output impedance of the oscillation circuit 15 is large. Therefore, when the output impedance of the oscillation circuit 15 is sufficiently small, the provision of the third resistor 14 is not necessarily needed.

In determining a resistance value of the second resistor 17, the electrodes 11 and 12 to be used actually are selected, and the mixed fuel conductivity is varied by the addition of NaCl aqueous solution, etc., whereby a combination which shows a smallest influence of the addition of NaCl aqueous solution, etc. on a change of the inclination of the differential waveform signal, is selected. When the mixed fuel conductivity is increased and the value of the resistance between the electrodes 11 and 12 becomes R, the dielectric dissipation factor tan $\delta$ of the capacitor formed between the electrodes 11 and 12 is represented as tan $\delta = 1/(\omega C R)$ (where C is the capacitance of the capacitor formed between the electrodes 11 and 12). Therefore, the dielectric dissipation factor tan $\delta$ is increased as R is decreased, and tan $\delta$ assumes about 3, when R = 10 K$\Omega$.

Figure 5:
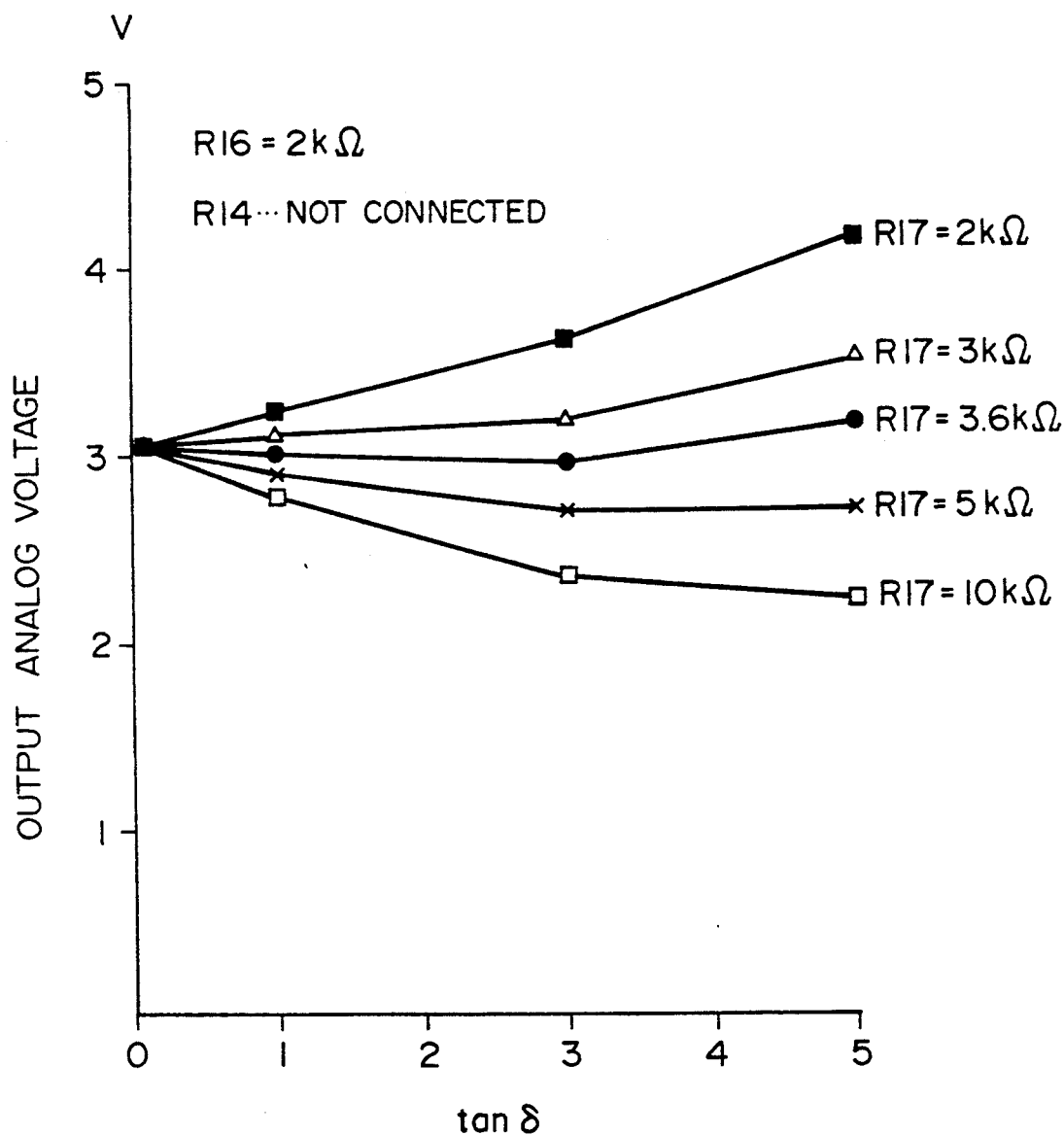
FIG. 5 is a characteristic diagram showing the relationship between the mixed fuel conductivity (represented by a loss in the electrode capacitor) and an output analog voltage, with resistance values of the second resistor (R17) used as a parameter.

FIG. 5 is a characteristic diagram showing the relationship between the resistance value R17 of the second resistor 17 and the dielectric dissipation factor tan $\delta$. Here, the value of the resistance between the electrodes 11 and 12 is about 10 K$\Omega$ when tan $\delta = 3$. From FIG. 5, it is understood that, if the resistance value of the first resistor 16 is 2 K$\Omega$ and that of the second resistor 17 is 3.6 K$\Omega$, the output analog voltage level becomes flat.

Figure 6:
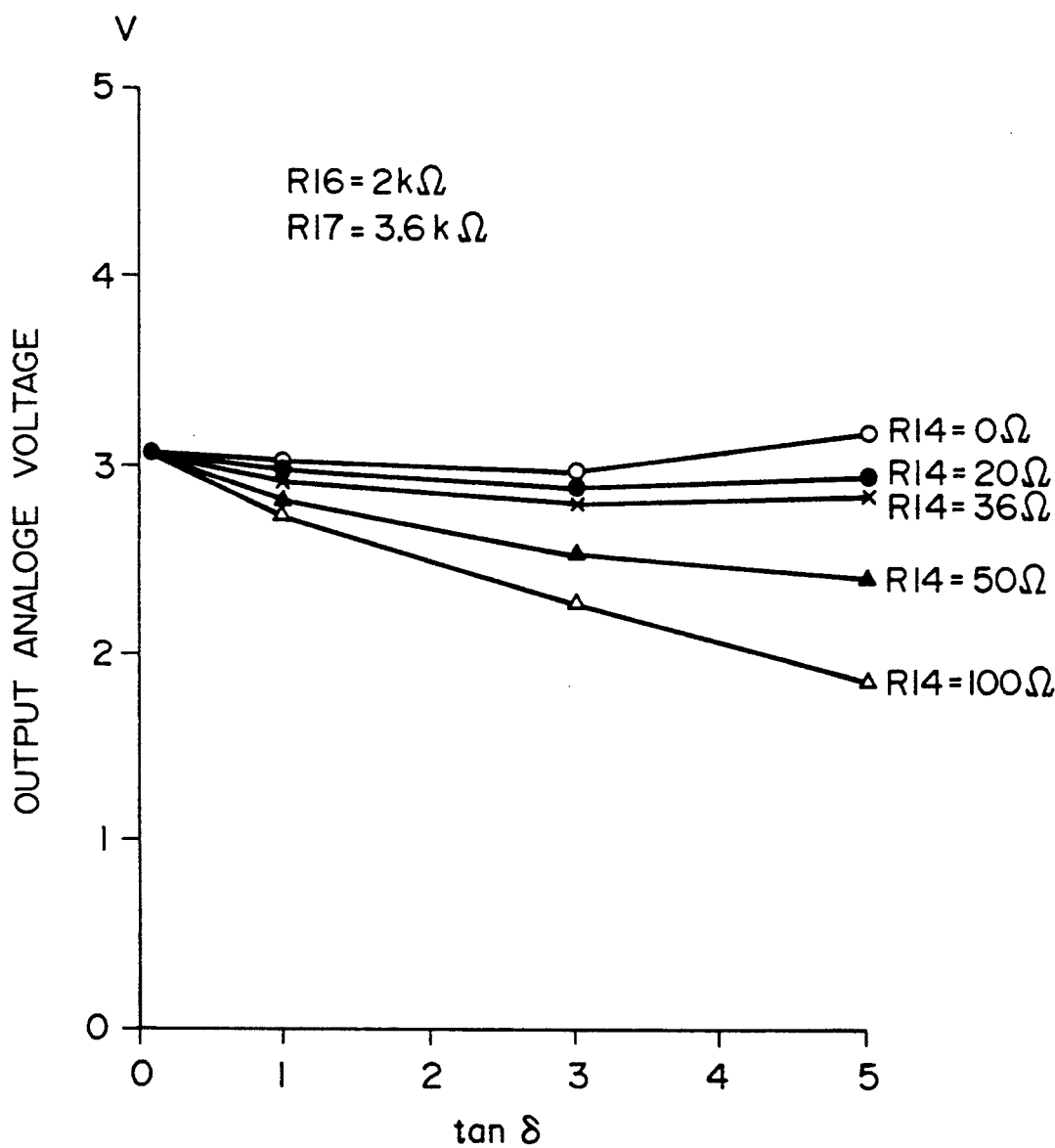
FIG. 6 is a characteristic diagram showing the relationship between the mixed fuel conductivity (represented by a loss in the electrode capacitor) and an output analog voltage, with resistance values of the third resistor (R14) used as a parameter, when the oscillation frequency of the oscillation circuit 15 is 2 MHz.
Figure 7:
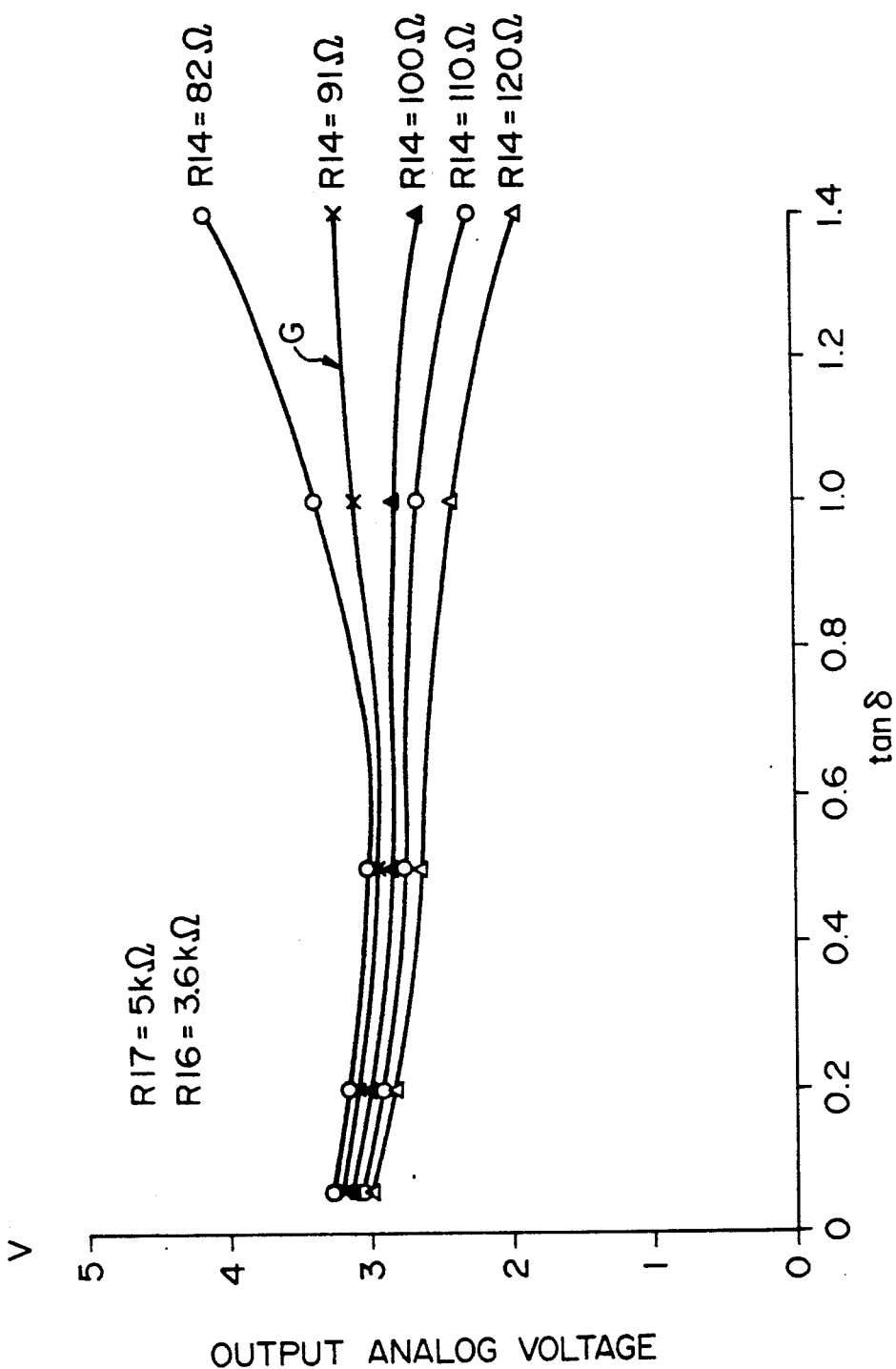
FIG. 7 is a characteristic diagram showing the relationship between the mixed fuel conductivity (represented by a loss in the electrode capacitor) and an output analog voltage, with resistance values of the third resistor (R14) used as a parameter, when the oscillation frequency of the oscillation circuit 15 is 100 KHz.

FIG. 6 is a characteristic diagram showing the relationship between the resistance value R14 of the third resistor 14 and the dielectric dissipation factor tan $\delta$. Here, the value of the resistance between the electrodes 11 and 12 is about 10 K$\Omega$ when tan $\delta = 3$. From FIG. 6, it is understood that, when the resistance value of the first resistor 16 is 2 K$\Omega$ and that of the second resistor 17 is 3.6 K$\Omega$, if the resistance value of the third resistor 14 is in the range of 0 to 50 $\Omega$, the output analog voltage level becomes flat. In this connection, in FIGS. 5 and 6, the output resistance of the final stage inverter IV4 of the oscillation circuit 15 is set to be about 50 $\Omega$. FIG. 7 is a characteristic diagram corresponding to FIG. 6, when the frequency of the oscillation circuit 15 is set to be 500 KHz.

Figure 8:
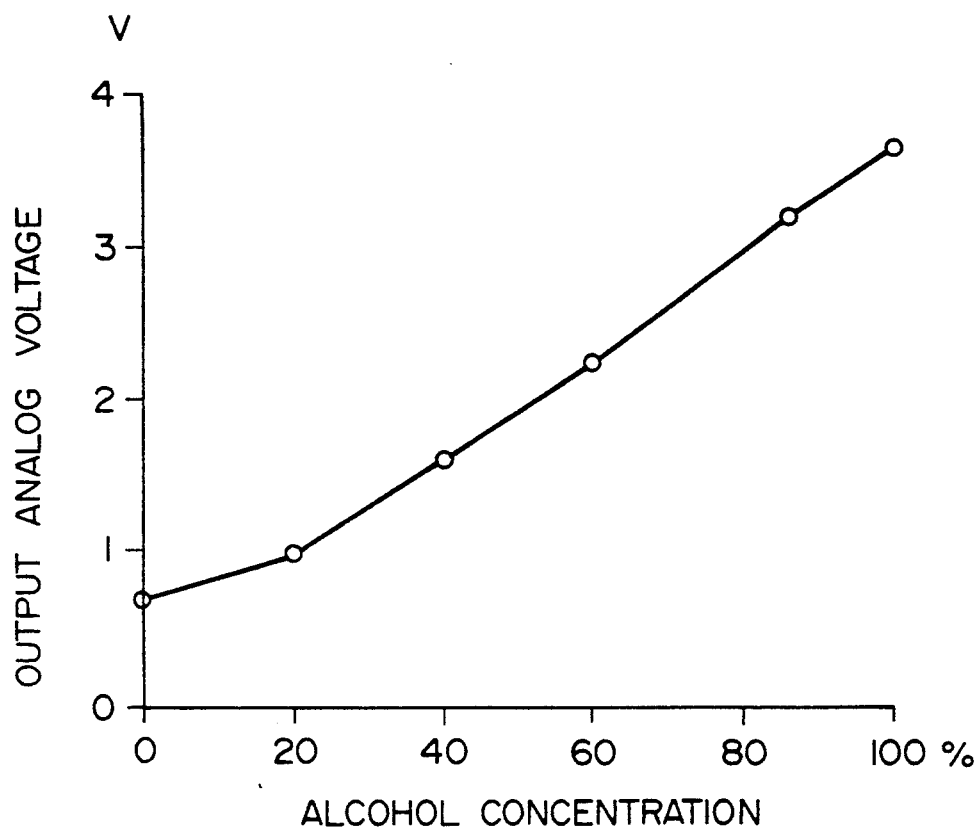
FIG. 8 is a characteristic diagram showing the relationship between the alcohol concentration and an output analog voltage in the circuit shown in FIG. 1.

In this way, it has been confirmed that, when the respective resistance values of the first, second and third resistors 16, 17 and 18, respectively, are selected in such a manner as shown in the characteristic diagram of FIG. 8, the substantially linear relationship can be obtained between the alcohol concentration and the output analog voltage. Thus, it is an important advantage of the present embodiment that a signal voltage proportional to an alcohol concentration is obtained with such a simple circuit arrangement. More precisely, with a conventional FM modulation apparatus, the oscillation frequency f is proportional to an inverse of square root of the capacitance (depending on the dielectric constant of the mixed fuel). Therefore, in order to obtain an output signal voltage proportional to an alcohol concentration, further complicated waveform conversion is required. According to the circuit of the present embodiment, a linear output can be obtained without resorting to such complicated waveform conversion.

Further, the oscillation frequency of the oscillation circuit 15 can be selected to be in the range of 500 KHz to 5 MHz. If the frequency is made higher, the influence of a change of the mixed fuel conductivity is reduced.

In addition, in the above-described embodiment, as the first resistor 16, a transistor or the like may be used instead of a resistor, the third resistor 14, the second resistor 17 and the capacitor 13 may be omitted, the diode 18 may also be omitted, and the oscillation circuit 15 may be a rectangular waveform oscillating circuit of the other type, such as a multivibrator or an operational amplifier, and may also be an oscillation circuit for producing an output signal having a waveform other than a rectangular waveform.

Further, instead of the inverters 19 and 20 which constitute the mixing ratio detecting means in the present invention, other analog-to-binary conversion circuits such as a Schmitt trigger circuit or a comparator may be adopted, and any other circuit corresponding to a circuit utilizing an inclination rate of the differential waveform signal may also be employed in place thereof. Instead of the integrating circuit composed of the integrating resistor 21 and the integrating capacitor 23, another analog smoothing circuit may be employed, and besides a technique of subjecting an analog signal to digital conversion and performing time measurement may be used.

Besides, in the present embodiment, the second resistor 17 is connected in parallel with the electrodes 11 and 12 so as to suppress a phenomenon that an increase of the mixed fuel conductivity has an influence on the capacitance value of a capacitor formed between the pair of electrodes and deteriorates the range of a change of an inclination of the inclined waveform. That is, the provision of the second resistor 17 imparts a resistance component in parallel with the pair of electrodes, and with this resistance component, the functional effect of the pair of electrodes as a capacitor is intentionally reduced. As a result, a bad influence of deterioration of an inclination of the inclined waveform exerted by an increase of the mixed fuel conductivity is made unnoticeable with respect to a change of the inclination of the inclined waveform which is proportional to an alcohol concentration, so that a change of the capacitance value of a capacitor formed between the pair of electrodes may determine substantially the inclination rate of the inclined waveform.

Further, in the present embodiment, since the DC blocking capacitor prevents a DC current from flowing through the electrodes 11 and 12, corrosion of the electrodes 11 and 12 caused by the DC current flow can be prevented. Further, leakage of a DC current from the electrodes 11 and 12 to the pipeline and the tank (made of a metal) and resultant corrosion caused by this leakage current can also be prevented. Further, even if the oscillation circuit 15 and the other circuits should fail, no DC power supply voltage is applied to the electrode 11, and therefore high safety can be maintained.

Figure 9:
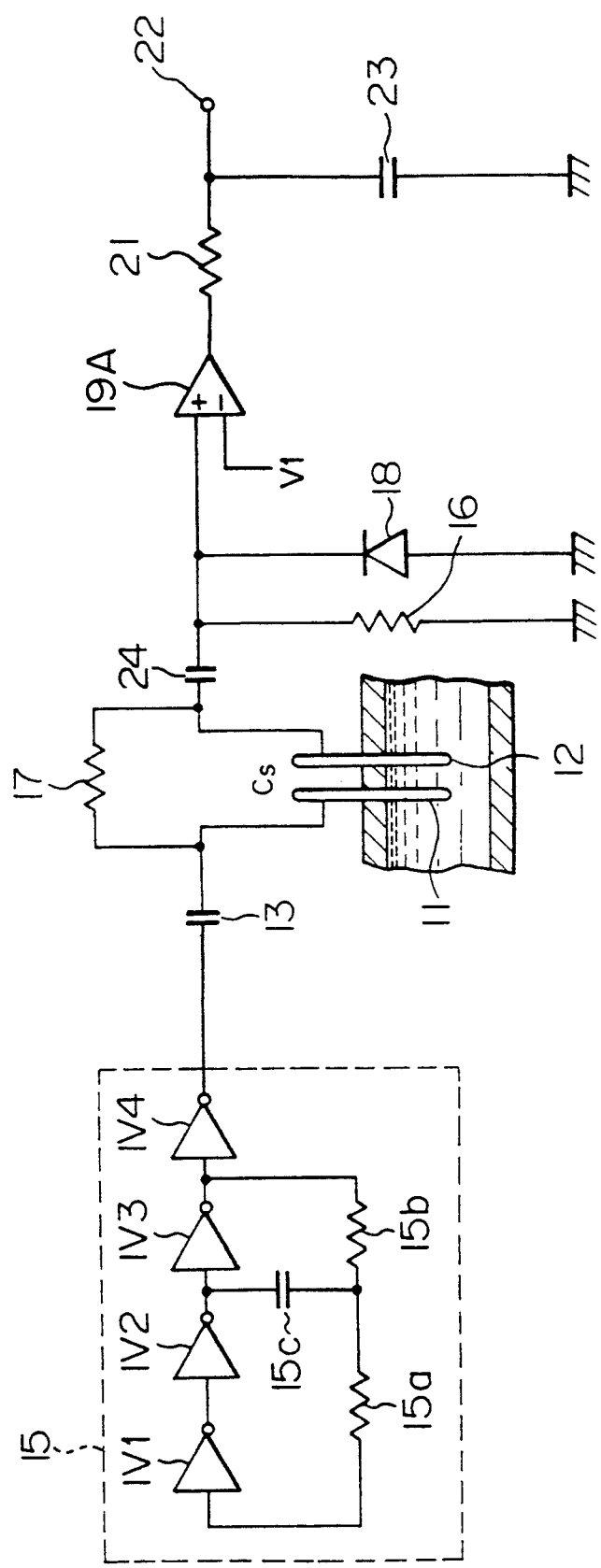
FIG. 9 is a circuit diagram showing the construction of a liquid mixing ratio detecting apparatus of a second embodiment of the present invention.

FIG. 9 is a circuit diagram showing the arrangement of a second embodiment of the present invention.

In this embodiment, the third resistor 14 is omitted, an AC coupling (DC blocking) capacitor 24 is added between the electrode 12 and the first resistor 16, and the inverters 19 and 20 are replaced with a comparator 19A. The capacitance value of the capacitor 24 is set to have a value approximately equal to that of the capacitor 13.

In this embodiment, since a DC current can be blocked more surely by the added capacitor 24 in conjunction with the capacitor 13 shown in the first embodiment, corrosion of the electrodes 11 and 12 caused by a DC current can be more surely prevented.

Moreover, in this embodiment, the electrode 11 is DC-blocked from the oscillation circuit, and the electrode 12 is DC-blocked from earth and from an input terminal of the comparator 19A. Therefore, even if DC potential of the respective opposite sides of the capacitors 24 and 13 are changed, no DC current flows between the electrodes 11, 12, and the pipeline and the tank (made of a metal). Besides, even if a DC voltage should be applied to the capacitor 24 due to a failure of the comparator 19A, it is possible to prevent a DC current from flowing through the electrode 12. Thus, any trouble such as electric discharge and resistance heating, which would be caused by accidental application of a DC voltage, can also be prevented.

In each of the above-mentioned embodiments, the electrode capacitor is used as a differentiating capacitor of the differentiating circuit. However, it may be used as an integrating capacitor. In this case, an end of an integrating resistor is connected in series with an output of the oscillation circuit, the other end of the integrating resistor is connected to an end of the AC coupling capacitor, and the other end of the Ac coupling capacitor is connected to an end of the electrode capacitor Cs, with the other end of the electrode capacitor Cs being connected to a reference potential point. Further, the second resistor is connected in parallel with the electrode capacitor Cs. Then, a resultant inclination rate signal of the integration waveform obtained by this arrangement is applied to the mixing ratio detection means which produces a mixing ratio signal. In this case, since the other end of the electrode capacitor Cs is grounded, fine adjustment of an output analog voltage by the third resistor cannot be performed. However, essential performance of this integrating circuit is substantially the same as that of the differentiating circuit.

We claim:

1. An apparatus for detecting a liquid mixing ratio comprising:
    a capacitor for detecting a mixing ratio composed of a pair of electrodes immersed with a predetermined distance kept therebetween in a mixed liquid containing a plurality of liquids having respective dielectric constants, which are different from each other, and arranged so that capacitance existing between the pair of electrodes varies depending on the mixing ratio of the mixed liquid;
    a resistor for constituting, in conjunction with said capacitor, one of a differentiating circuit and an integrating circuit;
    oscillation means for applying an oscillation signal of a fixed frequency to an input terminal of one of said differentiating circuit and integrating circuit; and
    mixing ratio detecting means for detecting an inclination rate signal relating to an inclination rate of one of a differential waveform and an integration waveform of the oscillation signal generated at an output terminal of one of said differentiating circuit and integrating circuit, respectively, and outputting a mixing ratio signal relating to the mixing ratio of the mixed liquid on the basis of the detected inclination rate signal.

2. An apparatus according to claim 1, further comprising a second resistor connected in parallel with said pair of electrodes.

3. An apparatus according to claim 1, wherein the mixed liquid is gasoline mixed with alcohol.

4. An apparatus for detecting a liquid mixing ratio comprising:
    a capacitor for detecting a mixing ratio composed of a pair of electrodes immersed with a predetermined distance kept therebetween in the mixed liquid containing a plurality of liquids having respective dielectric constants, which are different from each other, and arranged so that capacitance existing between said pair of electrodes varies depending on the mixing ratio of the mixed liquid;
    oscillation means for applying an oscillation voltage of a fixed frequency to one of said pair of electrodes;
    a resistor connected between the other of said pair of electrodes and a reference potential point and constituting, in conjunction with said capacitor, a differentiating circuit; and
    mixing ratio detecting means for detecting an inclination rate signal relating to an inclination rate of a differential waveform generated by said differentiating circuit and outputting a mixing ratio signal relating to the mixing ratio of the mixed liquid on the basis of the detected inclination rate signal.

5. An apparatus according to claim 4, further comprising a second resistor connected in parallel with said pair of electrodes.

6. An apparatus according to claim 4, wherein said oscillation means is composed of a rectangular waveform oscillation circuit, and said mixing ratio detecting means is composed of a comparator for producing, as the mixing ratio signal, a signal voltage of a magnitude proportional to a period of time between two points on the differential waveform having respective predetermined potentials equal to each other.

7. An apparatus according to claim 4, further comprising a third resistor connected between one of said pair of electrodes and an output terminal of said oscillation circuit.

8. An apparatus according to claim 4, further comprising a DC blocking capacitor connected between at least one of an output terminal of said oscillation circuit and said resistor, and a corresponding electrode of said pair of electrodes.

9. An apparatus according to claim 4, wherein the mixed liquid is gasoline mixed with alcohol.

* * * * *